United States Patent
Leysen et al.

(10) Patent No.: US 6,706,700 B2
(45) Date of Patent: Mar. 16, 2004

(54) 14β,15β-METHYLENE-17α-HYDROXYMETHYL-ANDROGENS

(75) Inventors: Dirk Leysen, Lommel (BE); Jaap Van der Louw, EN Oss (NL); Roberta Buma Bursi, HT s'Hertogenbosch (NL); Marcel Evert De Gooyer, RC Meteren (NL)

(73) Assignee: Akzo-Nobel, N.V. (NL)

( * ) Notice: Subject to any disclaimer, the term of this patent is extended or adjusted under 35 U.S.C. 154(b) by 0 days.

(21) Appl. No.: 10/148,820

(22) PCT Filed: Nov. 29, 2000

(86) PCT No.: PCT/EP00/12009

§ 371 (c)(1),
(2), (4) Date: Sep. 11, 2002

(87) PCT Pub. No.: WO01/40255

PCT Pub. Date: Jun. 7, 2001

(65) Prior Publication Data

US 2003/0100543 A1 May 29, 2003

(30) Foreign Application Priority Data

Dec. 2, 1999 (NL) .............................................. 99204080

(51) Int. Cl.[7] ........................... A61K 31/56; C07J 53/00
(52) U.S. Cl. ....................... 514/177; 514/178; 514/182; 552/510
(58) Field of Search ................................ 514/177, 178, 514/182; 552/510

(56) References Cited

U.S. PATENT DOCUMENTS 3,086,027 A   4/1963   Perelman

FOREIGN PATENT DOCUMENTS

| EP | 0 277 676 A | | 8/1988 |
| EP | 0768316 | * | 4/1997 |
| EP | 0 768 316 A | | 4/1997 |
| WO | 99 67276 A | | 12/1999 |
| WO | WO 99/67276 | * | 12/1999 |
| WO | 00 53619 A | | 9/2000 |

OTHER PUBLICATIONS

M A Avery et al: "Synthesis and testing of 17a.beta.–hydroxy–7.alpha.–methyl–D–homoes tr a–4, 16–dien–3one: a highly potent orally androgen" Steroids: Structure Function, and Regulation, US, Elsevier Science Publishers, New York, NY, vol. 55, No. 2, Feb. 1990, pp. 59–64.

Szpilfogel S A et al: "Steroid research at Organon in the golden 1950s and the following years" Steroids: Structure, Function, and Regulation, US, Elsevier Science Publishers, New York, NY, vol. 61, No. 8. Aug. 1, 1996, pp. 483–491.

R. Derman: "Androgens and Oral Contraception" Androgenic Disorders, 1995, pp. 301–323.

M.E. Wolf: "Burgers Medicinal Chemistry, Fourth Edition, Part II" 1979, John Wiley & Sons, New York, US p. 891–p. 916.

* cited by examiner

*Primary Examiner*—Barbara P. Badio
(74) *Attorney, Agent, or Firm*—Mark W. Minstead; William M. Blackstone

(57) ABSTRACT

The disclosed invention relates to the unexpected finding of novel steroids which are characterized by a 14β,15β-cyclopropane ring and a 17α hydroxymethyl group. These steroids according to the invention are found to have in common an androgenic activity. They can be used for the preparation of an agent for male contraception, as well as for the preparation of a medicament for the treatment of androgen insufficiency.

9 Claims, No Drawings

14β,15β-METHYLENE-17α-HYDROXYMETHYL-ANDROGENS

This application is a 371 of PCT/EP00/12009 filed Nov. 29, 2000.

The present invention is in the field of steroid compounds having a cyclopropane ring, which ring includes carbon atoms 14 and 15 of the steroid skeleton. More particularly, the invention pertains to such steroid compounds as possess an androgenic activity.

Steroids having the above-indicated cyclopropane ring have been disclosed in EP 768 316, which is in the field of female contraception and hormone-therapy against endometriosis or climacteric complaints. The steroids are described as having progestagenic activity, examples being 14α,15α-methylene estra-4,9-diene-3-one-17α-ol and 3-oxo 14β,15β-methylene estra-4,9-diene-17β-yl (N-phenyl)carbamate. Neither potency, nor any other receptor activities, of these progestagens can be derived from this disclosure.

In a non-prepublished patent application PCT/DE99/01795 (published on Dec. 29, 1999 as WO 99/67276) a group of 14,15-cyclopropyl steroids has been described, among which are 17β-hydroxy substituted ones.

Another non-prepublished patent application is WO 00/53619 wherein a group of androgenic steroids is described which have a 14β,17α configuration, viz. (14β,17α)-17-(hydroxymethyl) steroids.

The present invention now provides a novel group of steroids of the general type as indicated above, which possess an unexpected androgenic activity. Distinct from the progestagens disclosed in the art, the androgens of the present invention—including very potent ones—int.al. satisfy the requirements that the cyclopropane ring is β-oriented and that on carbon atom no. 17 a hydroxymethyl group is present which is α-oriented. As a consequence, the steroids of the invention have the 14β-configuration, contrary to natural steroid hormones, such as testosterone and estradiol, which have a configuration 14α, 17β.

The steroids according to the invention satisfy the structural formula I:

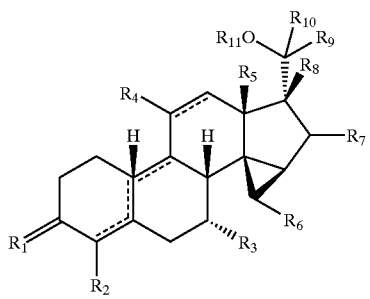

wherein
$R_1$ is O, (H,H), (H,OR), NOR, with R being hydrogen, $(C_{1-6})$ alkyl, $(C_{1-6})$ acyl;
$R_2$ is hydrogen, or $(C_{1-6})$ alkyl;
$R_3$ is hydrogen; or $R_3$ is $(C_{1-6})$ alkyl, $(C_{2-6})$ alkenyl, or $(C_{2-6})$ alkynyl, each optionally substituted by halogen;
$R_4$ is hydrogen, $(C_{1-6})$ alkyl, or $(C_{2-6})$ alkenyl;
$R_5$ is $(C_{1-6})$ alkyl;
$R_6$ is hydrogen, halogen, or $(C_{1-4})$ alkyl;
$R_7$ is hydrogen, or $(C_{1-6})$ alkyl;
$R_8$ is hydrogen, hydroxy, $(C_{1-6})$ alkoxy, halogen, or $(C_{1-6})$ alkyl;
$R_9$ and $R_{10}$ are independently hydrogen; or $R_9$ and $R_{10}$ are independently $(C_{1-6})$alkyl, $(C_{2-6})$ alkenyl, $(C_{3-6})$ cycloalkyl, $(C_{5-6})$ cycloalkenyl, or $(C_{2-6})$ alkynyl, each optionally substituted by $(C_{1-4})$ alkoxy, or halogen;
$R_{11}$ is hydrogen, $SO_3H$, $(C_{1-15})$ acyl; and the dotted lines indicate optional bonds, selected from a $\Delta^4$, $\Delta^{5(10)}$, or $\Delta^{11}$ double bond, or a $\Delta^{4,9}$ or $\Delta^{4,11}$ diene system.

The invention not only pertains to steroids which satisfy structural formula I, but also to pharmaceutically acceptable salts or esters, prodrugs and precursors thereof.

The term $(C_{1-6})$ alkyl as used in the definition of formula I means a branched or unbranched alkyl group having 1–6 carbon atoms, like methyl, ethyl, propyl, isopropyl, butyl, isobutyl, tertiary butyl, pentyl, and hexyl. Likewise, the term $(C_{1-4})$ alkyl means an alkyl group having 1–4 carbon atoms. Preferred alkyl groups have 1–4 carbon atoms, and most preferred alkyl groups are methyl and ethyl.

The term $(C_{2-6})$ alkenyl means a branched or unbranched alkenyl group having at least one double bond and 2–6-carbon atoms. Preferred alkenyl groups have 2–4 carbon atoms, such as vinyl and propenyl.

The term $(C_{2-6})$ alkynyl means a branched or unbranched alkynyl group having at least one triple bond and 2–6 carbon atoms. Preferred alkynyl groups have 2–4 carbon atoms, such as ethynyl and propynyl.

The term $(C_{3-6})$ cycloalkyl means a cycloalkane ring having 3–6 carbon atoms, like cyclopropane, cyclobutane, cyclopentane and cyclohexane.

The term $(C_{5-6})$ cycloalkenyl means a cycloalkene ring having at least one double bond and 5 or 6 carbon atoms.

The term $(C_{1-6})$ alkoxy means a branched or unbranched alkyloxy group having 1–6 carbon atoms, like methyloxy, ethyloxy, propyloxy, isopropyloxy, butyloxy, isobutyloxy, tertiary butyloxy, pentyloxy, and hexyloxy. Likewise, the term $(C_{1-4})$ alkoxy means a branched or unbranched alkyloxy group having 1–4 carbon atoms. Preferred alkyloxy groups have 1–4 carbon atoms, and most preferred is methyloxy.

The term $(C_{1-6})$ acyl means an acyl group derived from a carboxylic acid having 1–6 carbon atoms, like formyl, acetyl, propanoyl, butyryl, 2-methylpropanoyl, pentanoyl, pivaloyl, and hexanoyl. Likewise, the term $(C_{1-15})$ acyl means an acyl group derived from a carboxylic acid having 1–15 carbon atoms. Also included within the definition of $(C_{1-6})$ acyl or $(C_{1-15})$ acyl are acyl groups derived from dicarboxylic acids, like hemi-maloyl, hemi-succinoyl, hemi-glutaroyl, and so on.

The term halogen means fluorine, chlorine, bromine, or iodine. When halogen is a substituent at an alkyl group, like in the definition $R_3$, $R_6$, $R_8$, $R_9$ and $R_{10}$, Cl and F are preferred, F being most preferred.

The 14β,15β-methylene-17α-methanol steroid derivatives of this invention have the natural configurations 5α, 8β, 9α, 10β, and 13β. The configuration at C-17 is 17α. The compounds of the invention may possess also one or more additional chiral carbon atoms. They may therefore be obtained as a pure diastereomer, or as a mixture of diastereomers. Methods for obtaining the pure diastereomers are well known in the art, e.g. crystallization or chromatography.

For therapeutic use, salts of the compounds of formula I are those wherein the counterion is pharmaceutically acceptable. However, salts of the acids according to formula I may also find use, for example, in the preparation or purification of a pharmaceutically acceptable compound. All salts, whether pharmaceutically acceptable or not, are included within the ambit of the present invention. Examples of salts of acids according to the invention are mineral salts such as sodium salt, potassium salt, and salts derived from organic bases like ammonia, imidazole, ethylenediamine, triethylamine and the like.

The compounds of the invention as described hereinbefore in general possess an unexpected androgenic activity. Androgenic activity can be measured in various ways. Thus, the potency of androgens can be determined in vitro using the cytoplasmic androgen receptor from human breast tumor cells (MCF-7 cell line); see Bergink, E. W. et al, *Comparison of the receptor binding properties of nandrolone and testosterone under in vitro and in vivo conditions*, J. Steroid Biochem. 22, 831–836 (1985). It is also possible to use Chinese hamster ovary (CHO) cells transfected with the human androgen receptor (incubation time 16 h, temperature 4° C.) and compared with the affinity of 5α-dihydrotestosterone [according to the procedure described by Bergink, E. W. et al, J. Steroid Biochem. 19, 1563–1570 (1983)]. The transactivative androgen activity of the compounds of the invention can be measured, e.g. in Chinese hamster ovary cells (CHO) transfected with the human androgen receptor (hAR), in combination with a mouse mammary tumor virus (MMTV), and luciferase receptor gene (incubation time 16 h, temperature 37° C.) and compared with the activity of 5α-dihydrotestosterone [according to the procedure described by Schoonen, W. G. E. J. et al, Analyt. Biochem. 261, 222–224 (1998)]. For the in vivo potency determination of androgens the classical Hershberger test can be used. In this test the androgenic (increase in prostate weight) and anabolic activities [increase of the musculus levator ani (MLA)] of a compound are tested in immature castrated rats after daily administration for 7 days; see Hershberger, L. G. et al, *Myotrophic activity of 19-Nortestosterone and other steroids determined by modified levator ani muscle method*, Proceedings of the society for experimental biology and medicine 83, 175–180 (1953). Additionally, the effect of an androgenic compound on LH suppression can be tested in mature castrated rats according to Kumar, N. et al, *The biological activity of 7alpha-methyl-19-nortestosterone is not amplified in male reproductive tract as is that of testosterone*, Endocrinology 130, 3677–3683 (1992).

The preference goes to those compounds according to the invention which exhibit a relatively high androgenic activity. Thus, the preferred compounds of the invention are those satisfying the above structural formula I, wherein $R_1$ is oxo, and the dotted lines indicate a $\Delta^4$ double bond. More preferred are compounds wherein $R_3$ is 7α-methyl. A specifically preferred compound of the invention is (7α,14β,15β,17α)-17-(hydroxymethyl)-7-methyl-14,15-methyleneestr-4-en-3-one.

As androgenic hormones the steroids of the present invention can be used in, inter alia, male contraception and male HRT (hormone replacement therapy). Thus, e.g. male contraception may comprise a regimen of administration of hormones in which a progestagen serves to achieve a contraceptive effect and an androgen serves to supplement the resulting decreased testosterone level. Another option is that male contraception is performed with an androgenic hormone alone. The androgens can also be used for androgen supplementation in the partially androgen deficient ageing male. Next to the use in the male, the androgens of the invention also can be used in the female, e.g. as androgen replacement therapy in postmenopausal women, or in androgen-deficient children.

The present invention also relates to a pharmaceutical composition comprising a steroid compound according to the invention mixed with a pharmaceutically acceptable auxiliary, such as described in the standard reference, Gennaro et al, *Remmington's Pharmaceutical Sciences*, (18th ed., Mack Publishing Company, 1990, see especially Part 8: Pharmaceutical Preparations and Their Manufacture). The mixture of the steroid compounds according to the invention and the pharmaceutically acceptable auxiliary may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. nasal spray. For making dosage units, e.g. tablets, the use of conventional additives such as fillers, colorants, polymeric binders and the like is contemplated. In general any pharmaceutically acceptable additive which does not interfere with the function of the active compounds can be used. The steroid compounds of the invention may also be included in an implant, a vaginal ring, a patch, a gel, and any other preparation for sustained release.

Suitable carriers with which the compositions can be administered include lactose, starch, cellulose derivatives and the like, or mixtures thereof used in suitable amounts.

Furthermore, the invention relates to the use of the steroid compound according to the invention for the manufacture of a medicament in the treatment of androgen-deficiency, such as in male or female HRT (hormone replacement therapy). Accordingly, the invention also includes a method of treatment in the field of male or female HRT, comprising the administration to a male or female patient suffering from an androgen-deficiency, of a compound as described hereinbefore (in a suitable pharmaceutical dosage form).

Further, the invention relates to the use of a steroid compound according to the invention for the manufacture of a medicament having contraceptive activity (for which in the art the term "contraceptive agent" is also used). Thus the invention also pertains to the medical indication of contraception, i.e. a method of contraception comprising the administration to a subject, being a male, preferably a human male, of a compound as described hereinbefore (in a suitable pharmaceutical dosage form), in combined therapy with a progestagen or not.

The androgens according to the invention can also be used in a kit for male contraception. Although this kit can comprise one or more androgens only, it is preferred that it comprises means for the administration of a progestagen and means for the administration of an androgen.

The latter means is a pharmaceutical formulation comprising compound according to the invention as described hereinbefore, and a pharmaceutically acceptable carrier.

The invention also pertains to a method of treatment comprising administering to a (notably human) male or female in need of androgen-supplementation a therapeutically effective amount of a 14β,15β-methylene-17α-methanol steroid derivative as described hereinbefore. This is irrespective of whether or not the need for androgen-supplementation has arisen as a result of male contraception involving the administration of a sterilitant, such as a progestagen.

Further, the invention pertains to a method of contraception, comprising administering to a fertile male, notably human, a 14β,15β-methylene-17α-methanol steroid derivative as described hereinbefore in a dosage amount and regimen which is sufficient for said compound to be contraceptively effective per se. Alternatively, the method of contraception provided by the present invention comprises administering to a fertile male, notably human, a contraceptively effective combination of a sterilitant, such as a progestagen, and a 14β,15β-methylene-17α-methanol steroid derivative as described hereinbefore.

The compounds of the invention may be produced by various methods known in the art of organic chemistry in general, and especially in the art of the chemistry of steroids (see, for example: Fried, J. et al, *Organic Reactions in Steroid Chemistry*, Volumes I and II, Van Nostrand Reinhold Company, New York, 1972). Essential is the introduction of a 14β,15β-methylene group and a (substituted) 17α-(hydroxymethyl) group to the steroid nucleus.

A convenient starting material for the preparation of compounds of formula I wherein $R_1$ is oxo; $R_2$, $R_7$, $R_8$ and $R_{11}$ are hydrogen; $R_3$ and $R_4$ are hydrogen or ($C_{1-6}$) alkyl; $R_5$ is methyl; $R_6$, $R_9$ and $R_{10}$ have the previously given meaning; and the dotted lines indicate a $\Delta^4$ double bond, is for instance a compound of general formula II, wherein $R_3$ and $R_4$ are hydrogen or ($C_{1-6}$) alkyl, whose synthesis is known in literature, or which can be prepared using standard methods [see e.g. U.S. Pat. No. 3,407,217 (1965; $R_3$=H, $R_4$=H), FR 1434172 (1966; $R_3$=$CH_3$, $R_4$=H), DE 2539300 (1976; $R_3$=H, $R_4$=$CH_3$), WO 99/26962 ($R_3$=$CH_3$, $R_4$=$CH_3$)].

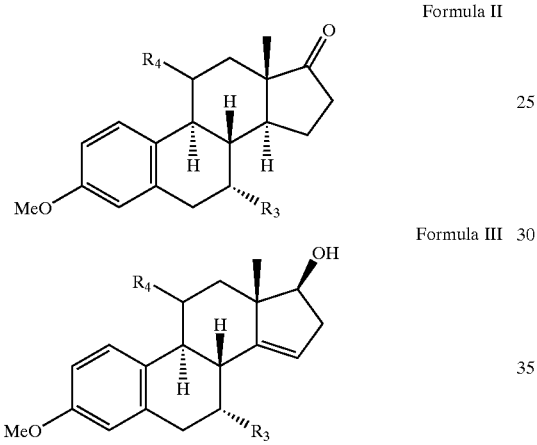

Formula II

Formula III

A possible synthesis route for compounds of the invention starts with the transformation of compounds of formula II into $\Delta^{14}$-compounds of formula III using methods described in WO 00/53619. Addition of a suitable carbene intermediate to the $\Delta^{14}$ double bond results in a (14β,15β,17β)-3-methoxy-14,15-methyleneestra-1,3,5(10)-trien-17-ol derivative [Helquist. P., in Comprehensive Organic Synthesis, Vol. 4, p. 951, Pergamon Press, Oxford, N.Y. (1991); Nair, V., ibid., Vol. 4, p. 999 (1991); Larock, R. C., *Comprehensive Organic Transformations*, VCH Publishers, Inc., 1989, p. 71]. Oxidation of the 17-hydroxy group produces a (14β,15β)-3-methoxy-14,15-methyleneestra-1,3,5(10)-trien-17-one derivative (for oxidations, see Hudlicky, M., *Oxidations in Organic Chemistry*, ACS Monograph 186, Washington, D.C., 1990) which serves as starting material for the introduction of the 17-carbinol fragment.

The conversion of 17-oxo to 17-($CH_2OH$) can be accomplished in several ways:

(a) 1: Wittig or Peterson reaction to a 17-methyleneestra-1,3,5(10)-triene derivative [Maercker, A., in Org. Reactions 14, p. 270, Wiley, New York, 1965; Ager, D. J., in Org. Reactions 38, p. 1, Wiley, New York, 1990]; 2: hydroboration, for instance by use of 9-BBN, disiamylborane, or thexylborane [see e.g. Zweifel, G. et al, in Org. Reactions 13, p. 1, Wiley, New York, 1963], resulting in the formation of a (17α)-estra-1,3,5(10)-triene-17-methanol derivative and/or the corresponding 17β isomer.

(b) 1: Conversion of the 17-ketone to a (17β)-spiroestra-1,3,5(10)-triene[17,2']oxirane by reaction with e.g. trimethylsulfonium iodide/n-BuLi [Corey, E. J. et al, J. Am. Chem. Soc. 87, 1353 (1965)]; 2: (Lewis)acid-catalyzed isomerization of the 17β-oxirane to 17α-formyl [Rickborn, B., in Comprehensive Organic Synthesis, Vol. 3, p. 733, Pergamon Press, Oxford, N.Y. (1991)]; 3: reduction of 17α-formyl to 17α-($CH_2OH$).

(c) 1: Conversion of the 17-ketone to a 17-methylene compound; 2: epoxidation with e.g. a peroxy acid, such as m-chloroperbenzoic acid, to a (17β)-spiroestra-1,3,5(10)-triene[17,2']oxirane; 3: (Lewis)acid-catalyzed isomerization to 17α-formyl as described under (b); 4: reduction of 17α-formyl to 17α-($CH_2OH$).

(d) 1: Conversion of the 17-ketone to a 17β-oxirane as described under (b) and (c); 2: Lewis acid-catalyzed reduction to the 17-methanol steroid [using e.g. $NaBH_3CN/BF_3.Et_2O$, see: Tone, H. et al, Tetrahedron Lett. 28, 4569 (1987)].

(e) 1: Reaction of the 17-ketone to the 17-cyano steroid by reaction with tosylmethyl isocyanide [TosMIC, see Bull, J. R. et al, Tetrahedron 31, 2151 (1975)]; 2: reduction of the cyano group to formyl by diisobutylaluminum hydride; 3: reduction of the 17-formyl group to 17-($CH_2OH$).

(f) 1: Wittig condensation with $(Ph)_3P$=CHOMe; 2: hydrolysis of the resulting enol ether; 3: reduction of 17-formyl to 17-($CH_2OH$).

(g) 1: Conversion of the 17-ketone to a 17β-oxirane as described under (b) and (c); 2: elimination to a estra-1,3,5(10),16-tetraene-17-methanol derivative; 3: hydrogenation of the $\Delta^{16}$ double bond.

(h) 1: Conversion of the 17-ketone to the corresponding enol triflate [see e.g. Cacchi, S. et al, Tetrahedron Lett. 25, 4821 (1984)]; 2: palladium-catalyzed alkoxycarbonylation of the latter to a alkyl estra-1,3,5(10),16-tetraene-17-carboxylate [Cacchi, S. et al, Tetrahedron Lett. 26, 1109 (1985)]; 3: reduction of the latter to the corresponding 17-methanol derivative; 4: hydrogenation of the $\Delta^{16}$ double bond.

(i) 1: Conversion of the 17-ketone to a alkyl estra-1,3,5(10),16-tetraene-17-carboxylate as described under (h); 2: 1,4-reduction, e.g. by hydrogenation or by lithium or sodium in liquid ammonia, to a alkyl estra-1,3,5(10)-triene-17-carboxylate derivative; 3: reduction of the ester to 17-($CH_2OH$).

Some of these methods (e.g. b,c) result in the stereoselective formation of the 17α-($CH_2OH$) isomer. Others (e.g. a) may give mixtures which can be separated by chromatography or crystallization.

The (14β,15β,17α)-3-methoxy-14,15-methyleneestra-1,3,5(10)-triene-17-methanol derivatives thus obtained are subjected to Birch reduction and subsequent hydrolysis to produce the (14β,15β,17α)-17-(hydroxymethyl)estr-4-ene-3-one derivatives of the invention.

Optionally, a (14β,15β,17α)-3-methoxy-14,15-methyleneestra-1,3,5(10)-triene-17-carboxaldehyde mentioned above can be reacted with an (organometallic) compound of formula $R_9M$ in which $R_9$ has the previously given meaning except for hydrogen, and M is Li, Na, K, MgX, ZnX, $CeX_2$, $SiR_3$ or $SnR_3$, to produce a 17-($CHR_9OH$) derivative which is usually a mixture of C-20 epimers. The latter can be separated whereafter Birch reduction and hydrolysis as described above provides the (14β,15β,17α)-17-($CHR_9OH$)-14,15-methyleneestr-4-en-3-one derivatives of the invention in which $R_9$ has the previously given meaning except for hydrogen.

Optionally, a (14β,15β,17α)-17-(CHR₉OH)-3-methoxy-14,15-methyleneestra-1,3,5(10)-triene can be oxidized to obtain a 20-ketone which can then be reacted with an (organometallic) compound of formula R₁₀M, R₁₀ having the previously given meaning except for hydrogen, and M having the previously given meaning. In that case Birch reduction and hydrolysis will provide 17-(CR₉R₁₀OH) derivatives of the invention wherein R₉ and R₁₀ have the previously given meaning except for hydrogen.

Optionally, the 20-ketone can be reduced by reaction with LiAlH₄, NaBH₄ or other reducing agents. In that case, 17-(CHR₉OH) derivatives are obtained of inverted stereochemistry at C-20. Epimerization at C-20 can also be accomplished by means of a Mitsunobu reaction [Dodge, J. A. et al, Bioorg. & Med. Chem. Lett. 6, 1 (1996)], or by treatment with methanesulfonyl chloride or p-toluenesulfonyl chloride followed by reaction with an oxygen nucleophile [e.g. potassium superoxide, see Corey, E. J. et al, Tetrahedron Lett. 3183 (1975)]. Optionally, a (14β,15β,17α)-3-methoxy-14,15-methyleneestra-2,5(10)-diene-17-methanol derivative, i.e. the product obtained after the Birch reduction, can be oxidized to the corresponding 17-carboxaldehyde. Reaction with a compound of formula R₉M as described above and hydrolysis affords the 17-(CHR₉OH) derivatives of the invention as already described above. This reaction sequence allows the introduction of substituents R₉, and analogously, R₁₀, which would not survive a Birch reduction. Optionally, the 3-methoxy-2,5(10)-diene might also be converted to a more stable system, e.g. a 3,3-dimethoxyestr-5(10)-ene derivative or a estr-4-en-3-one cyclic 1,2-ethanediyl (dithio)acetal derivative, prior to oxidation and reaction with R₉M, and so on.

Compounds of formula I with substituents at C-3, C-4, C-7, C-11, C-13, C-1', C-16 and C-17 other than those described under the definition of formula II, or compounds with R₁₁ other than hydrogen, or compounds without double bonds in the steroid nucleus, or with unsaturations other than a Δ⁴ double bond, can be prepared as follows.

Compounds of the invention in which R₁ is (H,H), (H,OR), NOR, and R is H, (C₁₋₆) alkyl, or (C₁₋₆) acyl can be prepared from compounds of formula I in which R₁ is oxo.

Compounds in which R₂ is (C₁₋₆)alkyl are obtained from compounds of formula I in which R₂ is hydrogen.

Compounds with substituents R₃ other than hydrogen can be prepared from e.g. (7α,17β)-7-ethenyl-17-hydroxyestr-4-en-3-one which can be prepared by copper(I)-catalyzed 1,6-addition of vinyllithium or a vinylmagnesium compound to e.g. (17β)-17-(acetyloxy)estra-4,6-diene-3-one [Syntex, DE 1143199 (1963)]. Conversion to (7α)-7-ethenyl-3-methoxyestra-1,3,5(10)-trien-17-one and construction of the functionalized and/or unsaturated side-chain at C-7 from 7-ethenyl are carried out using standard methods, and introduction of the 14β,15β-methylene group and the side-chain at C-17 are accomplished as described above. The precise sequence of reaction steps needed for these operations, and for the Birch reduction and the hydrolysis of the resulting estra-2,5(10)-diene, is dictated by methods common in synthetic strategy.

Compounds with substituents R₄ other than hydrogen or (C₁₋₆) alkyl can be obtained from e.g. (11β)-11-(hydroxymethyl)-3-methoxyestra-1,3,5(10)-trien-17-one cyclic 1,2-ethanediyl acetal [van den Broek, A. J. et al, Steroids 30, 481 (1977)], or 3-methoxyestra-1,3,5(10)-triene-11,17-dione cyclic 17-(1,2-ethanediyl acetal) [van den Broek, A. J. et al, Recl. Trav. Chim. Pays-Bas 94, 35 (1975)].

Compounds in which R₅ is e.g. ethyl can be prepared from e.g. 13-ethylgon-4-ene-3,17-dione [Brito, M. et al, Synth. Comm. 26, 623 (1996)].

16-Substituted compounds can be obtained via alkylation at C-16 of a (14β,15β)-3-methoxy-14,15-methyleneestra-1,3,5(10)-trien-17-one derivative.

17β-Alkylated compounds of formula I can e.g. be obtained via alkylation of a alkyl (14β,15β,17α)-3-methoxy-14,15-methyleneestra-1,3,5(10)-triene-17-carboxylate. Compounds of formula I in which R₈ is hydroxy, (C₁₋₆) alkoxy, or halogen can be prepared from a (17β)-spiroestra-1,3,5(10)-triene[17,2']oxirane.

Compounds of the invention in which R₁₁ is SO₃H or (C₁₋₁₅) acyl are obtained from compounds of formula I in which R₁₁ is hydrogen.

Compounds of the invention without unsaturations in the steroid nucleus are produced from Δ⁴ compounds wherein R₁ is oxo.

Compounds of the invention having Δ⁵⁽¹⁰⁾ double bond, or a Δ⁴,⁹ diene system are produced from the Δ²,⁵⁽¹⁰⁾ dienes obtained after the Birch reduction.

Compounds having a Δ¹¹ double bond can be prepared from e.g. estra-4,11-diene-3,17-dione [Broess, A. I. A. et al, Steroids 57, 514 (1992)].

The invention will be further explained hereinafter with reference to the following Examples.

EXAMPLE 1

(7α,14β,15β,17α)-17-(Hydroxymethyl)-7-methyl-14,15-methyleneestr-4-en-3-one

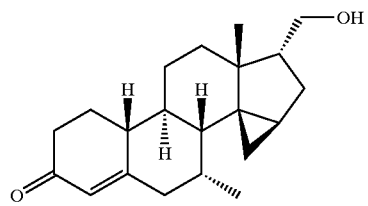

i)—A solution of (7α,17β)-3-methoxy-7-methylestra-1,3,5(10),14-tetraen-17-ol [Segaloff, A. et al, Steroids 22, 99 (1973); 25.4 g] and diiodomethane (27 ml) in dry dichloromethane (500 ml) was cooled to 0° C. A solution of diethylzinc in hexane (15% wt., 300 ml) was added in 1 h and the reaction mixture was stirred for 21 h at room temperature. Ice was added and the mixture was poured into a saturated aqueous solution of ammonium chloride. The product was extracted into diethyl ether; the combined organic phases were washed with brine, dried over sodium sulfate, and concentrated under reduced pressure. Column chromatography afforded (7α,14β,15β,17β)-3-methoxy-7-methyl-14,15-methyleneestra-1,3,5(10)-trien-17-ol (6.50 g).

ii)—A solution of the product obtained in the previous step (6.50 g) in acetone (325 ml), cooled to 5° C., was treated with Jones reagent (8 M, 11.9 ml). After 15 min. stirring at 5–10° C., 2-propanol was added and the mixture was filtered. The filtrate was concentrated; water was added and the product was extracted into ethyl acetate. The combined organic phases were washed with brine, dried over sodium sulfate and concentrated under reduced pressure, to give (7α,14β,15β)-3-methoxy-7-methyl-14,15-methyleneestra-1,3,5(10)-trien-17-one (6.57 g). The product was used in the following step without further purification.

iii)—Potassium tert-butoxide (6.1 g) was added in portions to a solution of the product obtained in the previous step (3.81 g) in a mixture of dry tetrahydrofuran (26 ml) and dry dimethyl sulfoxide (65 ml), containing trimethylsulfonium iodide (8.4 g). The reaction mixture was stirred at room temperature for 3 h and then poured into an aqueous solution of ammonium chloride. The product was extracted into ethyl acetate; the combined organic phases were washed with brine, dried over sodium sulfate, and concentrated under reduced pressure, to obtain (7α,14β,15β,17β)-3-methoxy-7-methyl-14,15-methylenespiroestra-1,3,5(10)-triene[17,2']oxirane (3.76 g). The product was used in the following step without further purification.

iv)—A solution of the product obtained in the previous step (3.76 g) in 1,4-dioxane (113 ml) was treated with an aqueous solution of perchloric acid (70%, 1.80 ml). The reaction mixture was stirred at room temperature for 2 h and then treated with another portion of perchloric acid (0.36 ml). The mixture was stirred for another 2 h and then poured into a saturated aqueous solution of sodium hydrogencarbonate. The product was extracted into ethyl acetate; the combined organic phases were washed with brine, dried over sodium sulfate and concentrated under reduced pressure, to give (7α,14β,15β,17α)-3-methoxy-7-methyl-14,15-methyleneestra-1,3,5(10)-triene-17-carboxaldehyde (4.11 g). The product was used in the following step without further purification.

v)—A solution of the product obtained in the previous step (3.7 g) in dry tetrahydrofuran (24 ml) was added dropwise to an ice-cooled suspension of lithium aluminium hydride (1.90 g) in tetrahydrofuran (24 ml). After 1 h stirring, the reaction was quenched by addition of a saturated aqueous solution of sodium sulfate. Ethyl acetate was added, and the mixture was filtered over dicalite. The organic phase was separated from the aqueous phase and washed with brine, dried over sodium sulfate and concentrated under reduced pressure. Column chromatography afforded (7α,14β,15β,17α)-3-methoxy-7-methyl-14,15-methyleneestra-1,3,5(10)-triene-17-methanol (1.30 g).

vi)—The product obtained in the previous step (1.30 g) in dry tetrahydrofuran (27 ml) was added to a refluxing solution of lithium (0.82 g) in liquid ammonia (54 ml). The reaction mixture was stirred at reflux temperature for 45 min. tert-Butanol (2.7 ml) was added and the mixture was stirred for 30 min. Ethanol was added and the ammonia was allowed to evaporate. Water was added and the product was extracted into ethyl acetate. The combined organic phases were washed with a saturated aqueous solution of ammonium chloride and brine, dried over sodium sulfate and concentrated under reduced pressure, to give (7α,14β,15β,17α)-3-methoxy-7-methyl-14,15-methyleneestra-2,5(10)-diene-17-methanol (1.17 g). The product was used in the following step without further purification.

vii)—A solution of the product obtained in the previous step (1.17 g) in acetone (23 ml) was treated with hydrochloric acid (6 M, 2 ml). After 1.5 h stirring at room temperature, a saturated aqueous solution of sodium hydrogencarbonate was added and the product was extracted into ethyl acetate. The combined organic phases were washed with a brine, dried over sodium sulfate and concentrated under reduced pressure. Column chromatography afforded (7α,14β,15β,17α)-17-(hydroxymethyl)-7-methyl-14,15-methyleneestr-4-en-3-one (0.40 g). M.p. 137–140° C., [α]$_D^{20}$=+73.0° (c=1.00, dioxane), $^1$H NMR (CDCl$_3$) δ5.80 (bs, 1H), 3.69 (m, 1H), 3.50 (m, 1H), 1.09 (s, 3H), 0.62 (d, 3H, J=7.1 Hz), 0.47 (dd, 1H, J=8.3 and 5.1 Hz), 0.28 (dd, 1H, J=5.1 and 3.5 Hz).

EXAMPLE 2

(7α,14,β15β,17α)-17-(Hydroxymethyl)-7-methyl-14,15-methyleneestr-5(10)-en-3-one

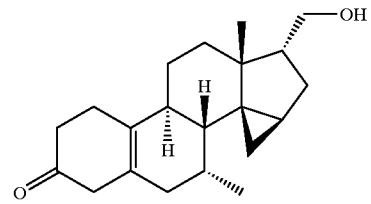

A solution of (7α,14β,15β,17α)-3-methoxy-7-methyl-14,15-methyleneestra-2,5(10)-diene-17-methanol (Example 1, step vi; 7.38 g) in a mixture of methanol (68 ml) and tetrahydrofuran (48 ml) was treated with a solution of oxalic acid (2.38 g) in water (40 ml). After 1 h stirring at room temperature, the reaction mixture was poured into a saturated aqueous solution of sodium hydrogencarbonate and the product was extracted into ethyl acetate. The combined organic phases were washed with brine, dried over sodium sulfate and concentrated under reduced pressure. Column chromatography afforded (7α,14β,15β,17α)-17-(hydroxyethyl)-7-methyl-14,15-methyleneestr-5(10)-en-3-one (4.27 g). $^1$H NMR (CDCl$_3$) δ3.69 (m, 1H), 3.51 (t, 1H, J=9.0 Hz), 2.72 (bs, 2H), 2.46 (bs, 2H), 1.04 (s, 3H), 0.69 (d, 3H, J=7.1 Hz), 0.48(dd, 1H, J=8.3 and 5.1 Hz), 0.27 (dd, 1H, J=5.1 and 3.1 Hz).

EXAMPLE 3

(7α,14β,15β17α)-17-(Hydroxymethyl)-7-methyl-14,15-methyleneestra-4,9-dienes-3-one

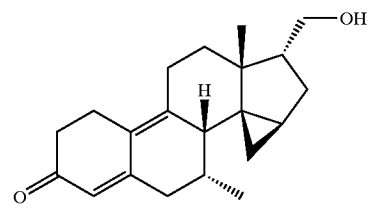

Phenyltrimethylammonium tribromide (1.01 g) was added to a solution of (7α,14β,15β,17α)-17-(hydroxymethyl)-7-methyl-14,15-methyleneestr-5(10)-en-3-one (Example 2, 0.85 g) in dry pyridine (25 ml). After 1.5 h stirring at room temperature the mixture was poured into ice-water and the product was extracted into ethyl acetate. The combined organic phases were washed with a saturated aqueous solution of sodium thiosulfate and brine, dried over sodium sulfate and concentrated under reduced pressure. Column chromatography provided (7α,14β,15β,17α)-17-(hydroxymethyl)-7-methyl-14,15-methyleneestra-4,9-dien-3-one (0.18 g). $^1$H NMR (CDCl$_3$) δ5.68 (s, 1H), 3.72 (m, 1H), 3.60 (m, 1H), 3.01 (bs, 1H), 1.11 (s, 3H), 0.69 (d, 3H, J=7.1 Hz), 0.52 (dd, 1H, J=8.3 and 5.5 Hz), 0.38 (dd, 1H, J=5.5 and 3.9 Hz).

EXAMPLE 4
(7α,14β,15β,17α)-17-(Hydroxymethyl)-4,7-dimethyl-14,15-methyleneestr-4-en-3-one

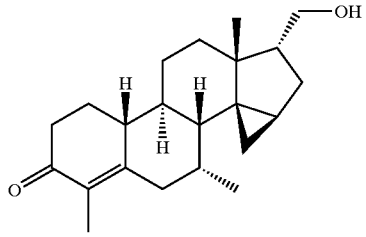

i)—A solution of (7α,14β,15β,17α)-17-(hydroxymethyl)-7-methyl-14,15-methyleneestr-4-en-3-one (Example 1, 0.40 g) in a mixture of formaldehyde (37 wt. % solution in water, 0.24 ml), triethylamine (0.288 ml), thiophenol (0.276 ml) and ethanol (0.721 ml) was stirred at room temperature overnight. The reaction mixture was poured into a aqueous solution of potassium hydroxide (0.5 M) and the product was extracted into ethyl acetate. The combined organic phases were washed with a aqueous solution of potassium hydroxide (0.5 M) and brine, dried over sodium sulfate and concentrated under reduced pressure. Column chromatography afforded (7α,14β,15β,17α)-17-(hydroxymethyl)-7-methyl-4-[(phenylthio)methyl]-14,15-methyleneestr-4-en-3-one (0.13 g).

ii)—A solution of the product obtained in the previous step (0.13 g) in acetone (4.8 ml) was treated with Raney-nickel (suspension in ethanol, 0.5 ml) and the mixture was heated at reflux temperature for 45 min. The mixture was filtered and the filtrate was concentrated under reduced pressure. Column chromatography afforded (7α,14β,15β,17α)-17-(hydroxymethyl)-4,7-dimethyl-14,15-methyleneestr-4-en-3-one (0.050 g). $^1$H NMR (CDCl$_3$) δ3.69 (dt, part A of AB system, 1H, J=10.6 and 5.1 Hz), 3.50 (ddd, part B of AB system, 1H, J=10.6, 8.3 and 4.7 Hz), 2.76 (dd, 1H, J=13.4 and 3.1 Hz), 1.78 (t, 3H, J=1.2 Hz), 1.08 (s, 3H), 0.61 (d, 3H, J=7.1 Hz), 0.47 (dd, 1H, J=8.3 and 5.1 Hz), 0.27 (dd, 1H, J=5.1 and 3.5 Hz).

EXAMPLE 5
(7α,14β,15β,17α)-7-Ethyl-17-(hydroxymethyl)-14,15-methyleneestr-4-en-3-one

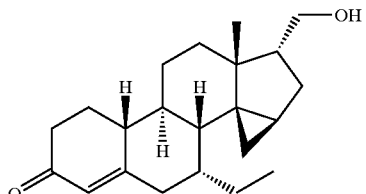

i)—Chlorotrimethylsilane (19 ml) was added in 5 min. to a suspension of (17α)-17-hydroxy-19-norpregna-4,6-dien-20-yn-3-one [Syntex S. A., GB 935116 (1958); 18.0 g] in a mixture of dichloromethane (300 ml) and pyridine (25 ml), cooled to 0° C. After 2 h stirring at 0° C. the reaction mixture was poured into a saturated aqueous solution of sodium hydrogencarbonate. The product was extracted into dichloromethane; the combined organic phases were washed with water and brine, dried over sodium sulfate and concentrated under reduced pressure, to afford (17α)-17-[(trimethylsilyl)oxy]-19-norpregna-4,6-dien-20-yn-3-one (22.3 g). The product was used in the following step without further purification.

ii)—A mixture of lithium (5.0 g) and dry diethyl ether (200 ml) was cooled to −30° C. Bromoethane (26.9 ml) was added dropwise whereafter the resulting solution of ethyllithium was transferred to a suspension of copper(I) iodide (30.6 g) in dry tetrahydrofuran (140 ml), cooled to −30° C. The resulting cuprate solution was stirred for 45 min. at that temperature and a solution of the product obtained in the previous step (20.0 g) in dry tetrahydrofuran (160 ml) was added dropwise. After 45 min. stirring at −25° C., chlorotrimethylsilane (20 ml) was added and stirring was continued for another 30 min. The reaction mixture was poured into a saturated aqueous solution of ammonium chloride and the product was extracted into ethyl acetate. The combined organic phases were washed with a saturated aqueous solution of ammonium chloride and brine, dried over sodium sulfate and concentrated under reduced pressure, to give (7α,17α)-7-ethyl-3,17-bis[(trimethylsilyl)oxy]-19-norpregna-3,5-dien-20-one (29.5 g). The product was used in the following step without further purification.

iii)—A solution of the product obtained in the previous step (29.5 g) in acetone (400 ml) was treated with hydrochloric acid (2.3 M, 20 ml). After 1.5 h stirring at room temperature, the reaction mixture was neutralized with a saturated aqueous solution of sodium hydrogencarbonate. The acetone was removed under reduced pressure and the product was extracted into ethyl acetate. The combined organic phases were washed with brine, dried over sodium sulfate and concentrated under reduced pressure, to give (7α,17α)-7-ethyl-17-hydroxy-19-norpregn-4-en-20-yn-3-one (19.5 g). The product was used in the following step without further purification.

iv)—Hydrochloric acid (6 M, 240 ml) was added dropwise to a suspension of dicalite (240 g) in methanol (1200 ml). After 20 min. stirring at room temperature the dicalite was collected by fitration and washed with water until neutral. Then, it was suspended in water (960 ml). With vigorous stirring, copper(II) nitrate trihydrate (145 g) was added, followed by careful addition of a solution of sodium carbonate (72.2 g) in water (360 ml). After 30 min. stirring, the product was collected by filtration and washed with water until neutral. The product was dried at 80° C. under reduced pressure, to give copper(II) carbonate on dicalite (310 g). A mixture of the product obtained under iii (19.5 g) and copper(II) carbonate on dicalite (70 g) in toluene (330 ml) was heated at reflux temperature for 9 h under removal of water by use of a Dean-Stark trap. The reaction mixture was filtered, the residue thoroughly washed with ethyl acetate, and the filtrate was concentrated under reduced pressure. Column chromatography gave (7α)-7-ethylestr-4-ene-3,17-dione (9.14 g).

v)—A solution of the product obtained in the previous step (9.14 g), copper(II) bromide (13.6 g), and lithium bromide (2.64 g) in acetonitrile (285 ml) was stirred at room temperature for 4 h. The reaction mixture was poured into water and the product extracted into ethyl acetate. The combined organic phases was washed with a saturated aqueous solution of ammonium chloride and brine, dried over sodium sulfate and concentrated under reduced pressure. Column chromatography afforded (7α)-7-ethyl-3-hydroxyestra-1,3,5 (10)-trien-17-one (6.54 g).

vi)—A mixture of the product obtained in the previous step (6.54 g), dry potassium carbonate (18.6 g), iodomethane (5.6 ml), and dry dimethylformamide (22 ml) was stirred at room temperature for 3.5 h. The reaction mixture was poured into water and the product extracted into ethyl acetate. The combined organic phases were washed with water, a saturated aqueous solution of ammonium chloride and brine, dried over sodium sulfate and concentrated under reduced pressure, to give (7α)-7-ethyl-3-methoxyestra-1,3,5 (10)-trien-17-one (6.77 g). The product was used in the following step without further purification.

vii)—A solution of diisopropylamine (6.15 ml) in dry tetrahydrofuran (70 ml) was cooled to −30° C. n-BuLi (1.6 M solution in hexanes, 27.5 ml) was added dropwise and stirring was continued for 30 min. The reaction mixture was cooled to −50° C. and a solution of the product obtained in the previous step (6.95 g) in dry tetrahydrofuran (100 ml) was added dropwise. Stirring was continued for 1 h. After cooling to −60° C., chlorotrimethylsilane (11.1 ml) was added. The mixture was stirred for 20 min. and then treated with a solution of phenyltrimethylammonium tribromide (10.0 g) in dry pyridine (31 ml). After 1 h stirring at −60° C., the mixture was poured into water and the product was extracted into ethyl acetate. The combined organic phases were washed with a saturated aqueous solution of sodium hydrogencarbonate and brine, dried over sodium sulfate and concentrated under reduced pressure. Column chromatography afforded (7α,16α)-16-bromo-7-ethyl-3-methoxyestra-1,3,5(10)-trien-17-one (8.75 g).

viii)—A mixture of the product obtained in the previous step (8.75 g), lithium bromide (12.7 g) and lithium carbonate (10.9 g) in dry dimethylformamide (77 ml) was heated under reflux for 3.25 h. After cooling, the reaction mixture was poured into water and the product was extracted into ethyl acetate. The combined organic phases were washed with water and brine, dried over sodium sulfate and concentrated under reduced pressure. Column chromatography afforded (7α)-7-ethyl-3-methoxyestra-1,3,5(10),14-tetraen-17-one (4.31 g) and (7α,14β)-7-ethyl-3-methoxyestra-1,3,5(10),15-tetraen-17-one (1.0 g).

ix)—A solution of sodium borohydride (0.21 g) and sodium hydroxide (0.44 g) in methanol (50 ml) was added dropwise to a solution of (7α)-7-ethyl-3-methoxyestra-1,3,5(10),14-tetraen-17-one (4.31 g) in dichloromethane (12 ml) and methanol (20 ml), cooled to 0° C. The reaction mixture was stirred for 1.5 h, quenched with acetone (4 ml), and then poured into a saturated aqueous solution of ammonium chloride. The product was extracted into ethyl acetate; the combined organic phases were washed with brine, dried over sodium sulfate and concentrated under reduced pressure, to give (7α,17β)-7-ethyl-3-methoxyestra-1,3,5(10),14-tetraen-17-ol (4.28 g). The product was used in the following step without further purification.

x)—Following a procedure analogous to that described under i of Example 1, the product obtained in the previous step (24.27 g) was converted to (7α,14β,15β,17β)-7-ethyl-3-methoxy-14,15-methyleneestra-1,3,5 (10)-trien-17-ol (12.82 g).

xi)—Following a procedure analogous to that described under ii of Example 1, the product obtained in the previous step (14.03 g) was converted to (7α,14β,15β)-7-ethyl-3-methoxy-14,15-methyleneestra-1,3,5(10)-trien-17-one (7.34 g).

xii)—Following a procedure analogous to that described under iii of Example 1, the product obtained in the previous step (6.80 g) was converted to (7α,14β,15β,17β)-7-ethyl-3-methoxy-14,15-methylenespiroestra-1,3,5(10)-triene[17,2']oxirane (7.24 g).

xiii)—Following a procedure analogous to that described under iv of Example 1, the product obtained in the previous step (7.24 g) was converted to (7α,14β,15β,17α)-7-ethyl-3-methoxy-14,15-methyleneestra-1,3,5 (10)-triene-17-carboxaldehyde (8.48 g).

xiv)—Following a procedure analogous to that described under v of Example 1, the product obtained in the previous step (8.48 g) was converted to (7α,14β,15β,17α)-7-ethyl-3-methoxy-14,15-methyleneestra-1,3,5 (10)-triene-17-methanol (1.23 g).

xv)—Following a procedure analogous to that described under vi of Example 1, the product obtained in the previous step (1.23 g) was converted to (7α,14β,15β,17α)-7-ethyl-3-methoxy-14,15-methyleneestra-2,5 (10)-diene-17-methanol (1.19 g).

xvi)—Following a procedure analogous to that described under vii of Example 1, the product obtained in the previous step (1.19 g) was converted to (7α,14β,15β,17α)-7-ethyl-17-(hydroxymethyl)-14,15-methyleneestr-4-en-3-one (0.40 g). $^1$H NMR (CDCl$_3$) δ5.82 (m, 1H), 3.69 (dt, part A of AB system, 1H, J=10.6 and 5.5 Hz), 3.51 (ddd, part B of AB system, 1H, J=10.6, 7.9 and 4.7 Hz), 1.09 (s, 3H), 0.79 (t, 3H, J=7.5 Hz), 0.45 (dd, 1H, J=8.3 and 5.5 Hz), 0.27 (dd, 1H, J=5.5 and 3.5 Hz).

EXAMPLE 6

(7α,14β,15β,17α)-13-Ethyl-17-(hydroxymethyl)-7-methyl-14,15-methylenegon-4-en-3-one

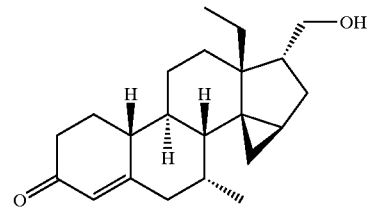

i)—Tetrapropylammonium perruthenate (1.3 g) was added to a solution of(7α,17β)-13-ethyl-3-methoxy-7-methylgona-1,3,5(10)-trien-17-ol [FRAD 87961 (1966); 19.5 g] and 4-methylmorpholine N-oxide (21.5 g) in acetone (513 ml). After 30 min. stirring at room temperature the reaction mixture was filtered over dicalite and silica. The filtrate was concentrated under reduced pressure. Column chromatography of the crude product gave (7α)-13-ethyl-3-methoxy-7-methylgona-1,3,5(10)-trien-17-one (11.0 g).

ii)—p-Toluenesulfonic acid (0.41 g) was added to a solution of the product obtained in the previous step (9.9 g) in a mixture of ethylene glycol (13.3 ml) and triethyl orthoformate (23.9 ml). The reaction mixture was stirred at room temperature for 3 h. Additional p-toluenesulfonic acid (0.41 g) was added and stirring was continued for 2 h. Water was added and stirring was continued for another 1 h. The product was extracted into ethyl acetate; the combined organic phases were washed with a saturated aqueous solution of sodium hydrogencarbonate and brine, dried over sodium sulfate and concentrated under reduced pressure, to give (7α)-13-ethyl-3-methoxy-7-methylgona-1,3,5(10)-trien-17-one cyclic 1,2-ethanediyl acetal and starting material (10.5 g, ratio 1:1). The procedure was repeated in order to achieve complete conversion of starting material. The product (9.8 g) was used in the following step without further purification.

iii)—Phenyltrimethylammonium tribromide (8.25 g) was added to a solution of the product obtained in the previous step (9.80 g) in dry tetrahydrofuran (55 ml). After 1 h stirring additional phenyltrimethylammonium tribromide (4.12 g) was added and stirring was continued for an additional 1 h. The reaction mixture was poured into a saturated aqueous solution of sodium thiosulfate. The product was extracted into ethyl acetate; the combined organic phases were washed with water and brine, dried over sodium sulfate and concentrated under reduced pressure, to give (7α,16α)-16-bromo-13-ethyl-3-methoxy-7-methylgona-1,3,5(10)-trien-17-one cyclic 1,2-ethanediyl acetal (14.5 g). The product was used in the following step without further purification.

iv)—A solution of the product obtained in the previous step (14.5 g) in dry dimethyl sulfoxide (55 ml) was treated with potassium tert-butoxide (12.4 g) and the reaction mixture was stirred at room temperature for 1.5 h. Additional potassium tert-butoxide (12.4 g) was added and the reaction mixture was stirred for another 3 h at 40° C. The mixture was poured into a saturated aqueous solution of ammonium chloride and the product was extracted into ethyl acetate. The combined organic phases were washed with water and brine, dried over sodium sulfate and concentrated under reduced pressure. Column chromatography afforded (7α)-13-ethyl-3-methoxy-7-methylgona-1,3,5(10),15-tetraen-17-one cyclic 1,2-ethanediyl acetal (6.30 g).

v)—A solution of the product obtained in the previous step (6.3 g) in dry toluene (162 ml) was treated with pyridinium p-toluenesulfonate (4.21 g) and heated under reflux for 1 h. After cooling, the reaction mixture was poured into a saturated aqueous solution of sodium hydrogencarbonate and the product was extracted into ethyl acetate. The combined organic phases were washed with brine, dried over sodium sulfate and concentrated under reduced pressure, to give (7α)-13-ethyl-3-methoxy-7-methylgona-1,3,5(10),14-tetraen-17-one cyclic 1,2-ethanediyl acetal (6.5 g). The product was used in the following step without further purification.

vi)—A solution of the product obtained in the previous step (6.5 g) in dry toluene (251 ml) was treated with p-toluenesulfonic acid (3.5 g) and heated under reflux for 45 min. After cooling, the reaction mixture was poured into a saturated aqueous solution of sodium hydrogencarbonate and the product was extracted into ethyl acetate. The combined organic phases were washed with water and brine, dried over sodium sulfate and concentrated under reduced pressure, to give (7α)-13-ethyl-3-methoxy-7-methylgona-1,3,5(10),14-tetraen-17-one (5.9 g). The product was used in the following step without further purification.

vii)—Following a procedure analogous to that described under v of Example 1, the product obtained in the previous step (5.9 g) was converted to (7α,17β)-13-ethyl-3-methoxy-7-methylgona-1,3,5(10),14-tetraen-17-ol (4.4 g).

viii)—Following a procedure analogous to that described under i of Example 1, the product obtained in the previous step (2.9 g) was converted to (7α,14β,15β,17β)-13-ethyl-3-methoxy-7-methyl-14,15-methylenegona-1,3,5(10)-trien-17-ol (1.4 g).

ix)—Following a procedure analogous to that described under ii of Example 1, the product obtained in the previous step (1.4 g) was converted to (7α,14β,15β)-13-ethyl-3-methoxy-7-methyl-14,15-methylenegona-1,3,5(10)-trien-17-one (1.4 g).

x)—Following a procedure analogous to that described under iii of Example 1, the product obtained in the previous step (1.3 g) was converted to (7α,14β,15β,17β)-13-ethyl-3-methoxy-7-methyl-14,15-methylenespirogona-1,3,5(10)-triene[17,2']oxirane (1.36 g).

xi)—Following a procedure analogous to that described under iv of Example 1, the product obtained in the previous step (1.36 g) was converted to (7α,14β,15β,17α)-13-ethyl-3-methoxy-7-methyl-14,15-methylenegona-1,3,5(10)-triene-17-carboxaldehyde (1.35 g).

xii)—Following a procedure analogous to that described under v of Example 1, the product obtained in the previous step (1.35 g) was converted to (7α,14β,15β,17α)-13-ethyl-3-methoxy-7-methyl-14,15-methylenegona-1,3,5(10)-triene-17-methanol (0.80 g).

xiii)—Following a procedure analogous to that described under vi of Example 1, the product obtained in the previous step (0.60 g) was converted to (7α,14β,15β,17α)-13-ethyl-3-methoxy-7-methyl-14,15-methylenegona-2,5(10)-diene-17-methanol (0.60 g).

xiv)—Following a procedure analogous to that described under vii of Example 1, the product obtained in the previous step (0.60 g) was converted to (7α,14β,15β,17α)-13-ethyl-17-(hydroxymethyl)-7-methyl-14,15-methylenegon-4-en-3-one (0.17 g). $^1$H NMR (CDCl$_3$) δ5.79 (bs, 1H), 3.73 (m, 1H), 3.47 (m, 1H), 0.92 (t, 3H, J=7.5 Hz), 0.59 (d, 3H, J=7.1 Hz). (dd, 1H, J=7.9 and 5.1 Hz), 0.41 (dd, 1H, J=5.1 and 3.5 Hz).

EXAMPLE 7

(7α,14β,15β16β,17α)-17-(Hydroxymethyl)-7,16-dimethyl-14,15-methyleneestra-4-en-3-one

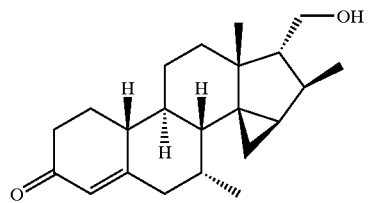

i)—A solution of lithium bis(trimethylsilyl)amide (20.2 mmol) in tetrahydrofuran (35 ml) was cooled to −40° C. A solution of (7α,14β,15β)-3-methoxy-7-methyl-14,15-methyleneestra-1,3,5 (10)-trien-17-one (Example 1, step ii; 5.60 g) in dry tetrahydrofuran (24 ml) was added dropwise and the reaction mixture was stirred for 30 min. Then, at −30° C., iodomethane (2.4 ml) was added and stirring was continued for 45 min. The mixture was poured into a saturated aqueous solution of ammonium chloride and the product was extracted into ethyl acetate. The combined organic phases were washed with brine, dried over sodium sulfate and concentrated under reduced pressure, to give (7α,14β, 15β,16α)-3-methoxy-7,16-dimethyl-14,15-methyleneestra-1,3,5(10)-trien-17-one (5.99 g). The product was used in the following step without further purification.

ii)—A mixture of methyltriphenylphosphonium bromide (17 g), potassium tert-butoxide (4.4 g) and dry toluene (173 ml) was heated under reflux for 1 h. A solution of the ketone obtained in the previous step (5.04 g) in dry toluene (40 ml) was added dropwise and heating was continued for 3 h. After cooling, the reaction mixture was poured into a saturated aqueous solution of ammonium chloride. The product was extracted into ethyl acetate; the combined organic phases were washed with brine, dried over sodium sulfate and concentrated under reduced pressure. Column chromatography afforded (7α,14β,15β,16β)-3-methoxy-7,16-dimethyl-17-methylene-14,15-methyleneestra-1,3,5(10)-triene (3.61 g).

iii)—m-Chloroperbenzoic acid (70–75%, 2.3 g) was added to a solution of the product obtained in the previous step (3.0 g) in dry dichloromethane (51 ml), containing solid sodium hydrogencarbonate (3 g). The reaction mixture was stirred at room temperature for 3 h; additional portions of m-chloroperbenzoic acid (70–75%, 0.77 g) were added after 1 h and 2 h, respectively. The reaction was poured into a saturated aqueous solution of sodium sulfite and the product was extracted into dichloromethane. The combined organic phases were washed with a aqueous solution of sodium hydroxide (10%) and brine, dried over sodium sulfate and concentrated under reduced pressure, to give (7α, 14β,15β,16β,17β)-3-methoxy-7,16-dimethyl-14,15-methylenespiroestra-1,3,5(10)-triene[17,2']oxirane (2.85 g). The product was used in the next step without further purification.

iv)—Following a procedure analogous to that described under iv of Example 1, the product obtained in the previous step (2.85 g) was converted to (7α,14β,15β, 16β,17α)-3-methoxy-7,16-dimethyl-14,15-methyleneestra-1,3,5(10)-triene-17-carboxaldehyde (2.99 g).

v)—Following a procedure analogous to that described under v of Example 1, the product obtained in the previous step (2.99 g) was converted to (7α,14β,15β, 16β,17α)-3-methoxy-7,16-dimethyl-14,15-methyleneestra-1,3,5(10)-triene-17-methanol (0.30 g).

vi)—Following a procedure analogous to that described under vii of Example 1, the product obtained in the previous step (0.30 g) was converted to (7α,14β,15β, 16β,17α)-3-methoxy-7,16-dimethyl-14,15-methyleneestra-2,5(10)-diene-17-methanol (0.31 g).

vii)—Following a procedure analogous to that described under vii of Example 1, the product obtained in the previous step (0.31 g) was converted to (7α,14β,15β, 16β,17α-17-(hydroxymethyl)-7,16-dimethyl-14,15-methyleneestr-4-en-3-one (0.053 g). ¹H NMR (CDCl₃) δ5.80 (m, 1H), 3.64 (m, 2H), 1.09 (s, 3H), 1.01 (d, 3H, J=6.7 Hz), 0.62 (d, 3H, J=7.1 Hz). 0.38 (dd, 1H, J=7.9 and 5.1 Hz), 0.25 (dd, 1H, J=5.1 and 3.5 Hz).

EXAMPLE 8

(7α,14β,15β,17β)-17-Hydroxy-17-(hydroxymethyl)-7-methyl-14,15-methyleneestr-4-en-3-one

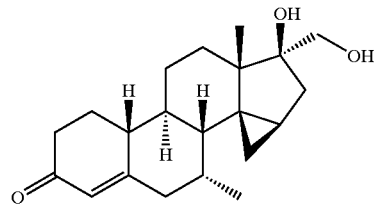

i)—Potassium hydroxide (3.28 g) was added to a solution of (7α,14β,15β,17β)-3-methoxy-7-methyl-14,15-methylenespiroestra-1,3,5(10)-triene[17,2']oxirane (Example 1, step iii; 5.00 g) in a mixture of dimethyl sulfoxide (147 ml) and water (25.3 ml). The reaction mixture was stirred at 100° C. overnight and then poured into a aqueous solution of ammonium chloride. The product was extracted into ethyl acetate; the combined organic phases were washed with brine, dried over sodium sulfate, and concentrated under reduced pressure. Column chromatography gave (7α,14β15β, 17β)-17-(hydroxymethyl)-3-methoxy-7-methyl-14,15-methylenesestra-1,3,5(10)-trien-17-ol (1.02 g).

ii)—Following a procedure analogous to that described under vi of Example 1, the product obtained in the previous step (1.02 g) was converted to (7α,14β,15β, 17β)-17-(hydroxymethyl)-3-methoxy-7-methyl-14,15-methyleneestra-2,5(10)-dien-17-ol (1.05 g).

iii)—Following a procedure analogous to that described under vii of Example 1, the product obtained in the previous step (1.05 g) was converted to (7α,14β, 15β17β)-17-hydroxy-17-(hydroxymethyl)-7-methyl-14,15-methyleneestr-4-en-3-one (0.12 g). ¹H NMR (CDCl₃) δ5.80 (bs, 1H), 3.63 (dd, part A of AB system, 1H, J=10.6 and 4.7 Hz), 3.46 (dd, part B of AB system, 1H, J=10.6 and 5.1 Hz), 1.11 (s, 3H), 1.10 (dd, 1H, J=4.7 and 3.9 Hz), 0.61 (d, 3H, J=7.1 Hz), 0.54 (dd, 1H, J=8.3 and 4.7 Hz).

EXAMPLE 9

(7α,14β,15β,17β)-17-[(Acetyloxy)methyl]-17-fluoro-7-methyl-14,15-methyleneestr-4-en-3-one a) and (7α,14β, 15β,17β)-17-fluoro-17-(hydroxymethyl)-7-methyl-14,15-methyleneestra-4-en-3-one (b)

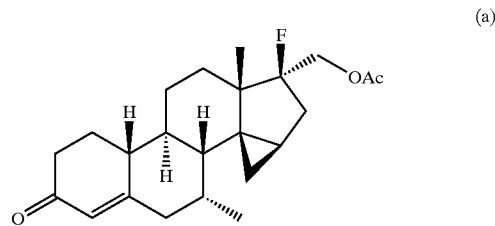

(a)

(b)

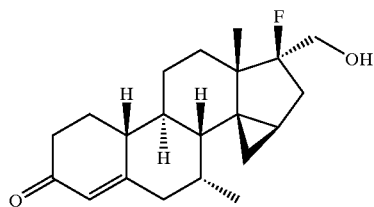

i)—A solution of (7α,14β,15β,17β)-3-methoxy-7-methyl-14,15-methylenespiroestra-1,3,5(10)-triene[17,2']oxirane (Example 1, step iii; 1.75 g) in dry diethyl ether (43.7), cooled to −10° C., was treated with boron trifluoride diethyl etherate (1.75 ml). The reaction mixture was stirred for 15 min. and then quenched with a saturated aqueous solution of sodium hydrogencarbonate. The product was extracted into ethyl acetate; the combined organic phases were washed with a saturated aqueous solution of sodium hydrogencarbonate and brine, dried over sodium sulfate, and concentrated under reduced pressure. Column chromatography afforded (7α,14β,15β,17β)-17-fluoro-3-methoxy-7-methyl-14,15-methyleneestra-1,3,5(10)-triene-17-methanol (0.36 g).

ii)—Following a procedure analogous to that described under vi of Example 1, the product obtained in the previous step (0.36 g) was converted to a mixture of (7α,14β,15β,17β)-17-fluoro-3-methoxy-7-methyl-14,15-methyleneestra-2,5(10)-diene-17-methanol and (7α,14β,15β,17α)-3-methoxy-7-methyl-14,15-methyleneestra-2,5(10)-diene-17-methanol (0.36 g, ratio 1:3).

iii)—Following a procedure analogous to that described under vii of Example 1, the mixture of products obtained in the previous step (0.36 g) was converted to (7α,14β,15β,17β)-17-fluoro-17-(hydroxymethyl)-7-methyl-14,15-methyleneestr-4-en-3-one and (7α,14β,15β,17α)-17-(hydroxymethyl)-7-methyl-14,15-methyleneestr-4-en-3-one (0.32 g, ratio 1:3).

iv)—A solution of the mixture obtained in the previous step (0.32 g) in a mixture of dry pyridine (1.50 ml) and dry tetrahydrofuran (5 ml), containing 4-(dimethylamino)pyridine (0.005 g) was treated with acetic anhydride (0.90 ml). The mixture was stirred at room temperature for 1.5 h and then quenched with ice-water, followed by addition of a saturated aqueous solution of sodium hydrogencarbonate. The product was extracted into ethyl acetate; the combined organic phases were washed with water, aqueous sulfuric acid (2 M) and brine, dried over sodium sulfate, and concentrated under reduced pressure. Column chromatography afforded (7α,14β,15β,17β)-17-[(acetyloxy)methyl]-17-fluoro-7-methyl-14,15-methyleneestr-4-en-3-one (0.050 g). $^1$H NMR (CDCl$_3$) δ5.81 (bs, 1H), 4.22 (dd, part A of AB system, 1H, J=22.8 and 12.2 Hz), 4.12 (dd, part B of AB system, 1H, J=22.4 and 12.2 Hz), 2.10 (s, 3H), 1.17 (d, 3H, J=2.8 Hz), 0.62 (d, 3H, J=7.1 Hz).

v)—A solution of the product obtained under iv (0.030 g) in methanol (1 ml) was treated with a solution of sodium hydroxide (0.009 g) in a mixture of methanol (0.3 ml) and water (0.03 ml). The reaction mixture was stirred at room temperature for 30 min. and poured into ice-water. The product was extracted into ethyl acetate; the combined organic phases were washed with brine, dried over sodium sulfate and concentrated under reduced pressure, to give (7α,14β,15β,17β)-17-fluoro-17-(hydroxymethyl)-7-methyl-14,15-methyleneestr-4-en-3-one (0.030 g). $^1$H NMR (CDCl$_3$) δ5.81 (bs, 1H), 3.74 (ddd, part A of AB system, 1H, J=20.4, 12.2 and 6.6 Hz), 3.60 (ddd, part B of AB system, 1H, J=22.8, 12.2 and 6.7 Hz), 1.15 (d, 3H, J=2.8 Hz), 0.62 (d, 3H, J=7.1 Hz); $^{19}$F NMR (CDCl$_3$) δ−156.08 (s).

EXAMPLE 10

(7α,14β,15β,17β)-17-[(Acetyloxy)methyl]-17-fluoro-7-methyl-14,15-methyleneestr-5(10)-en-3-one

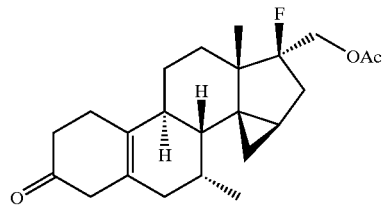

i)—Following a procedure analogous to that described under Example 2, the mixture of (7α,14β,15β,17β)-17-fluoro-3-methoxy-7-methyl-14,15-methyleneestra-2,5(10)-diene-17-methanol and (7α,14β,15β,17β)-3-methoxy-7-methyl-14,15-methyleneestra-2,5(10)-diene-17-methanol (0.076 g, ratio 1:3) (Example 9, step ii) was converted to a mixture of (7α,14β,15β,17β)-17-fluoro-17-(hydroxymethyl)-7-methyl-14,15-methyleneestr-5(10)-one and (7α,14β,15β,17β)-17-(hydroxymethyl)-7-methyl-14,15-methyleneestr-5(10)-en-3 (0.060 g, ratio 1:3).

ii)—Following a procedure analogous to that described under iv of Example 9, the mixture of products obtained under i (0.060 g) was acetylated and separated by column chromatography, to give (7α,14β,15β,17β)-17-[(acetyloxy)methyl]-17-fluoro-7-methyl-14,15-methyleneestr-5(10)-en-3-one (0.008 g). $^1$H NMR (CDCl$_3$) δ4.25 (dd, part A of AB system, 1H, J=23.6 and 12.2 Hz), 4.12 (dd, part B of AB system, 1H, J=22.4 and 12.2 Hz), 2.73 (bs, 2H), 2.09 (s, 3H), 1.12 (d, 3H, J=2.8 Hz), 0.69 (d, 3H, J=7.1 Hz).

EXAMPLE 11

(7α,14β,15β,17α,20S)-20-Hydroxy-7-methyl-14,15-methylene-19-norpregn-4-en-3-one (a) and (7α,14β,15β,17α,20R)-20-hydroxy-7-methyl-14,15-methylene-19-norpregn-4-en-3-one (b)

20S

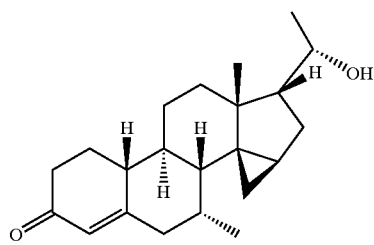

20R

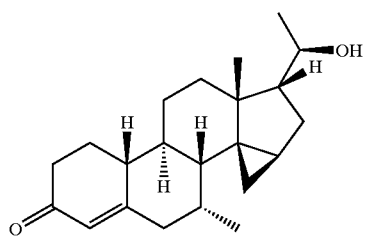

i)—A solution of (7α,14β,15β,17α)-3-methoxy-7-methyl-14,15-methyleneestra-1,3,5(10)-triene-17-carboxaldehyde (Example 1, step iv; 2.50 g) in dry tetrahydrofuran (15.4 ml), cooled to 0° C., was treated with methylmagnesium chloride (1.5 M solution in tetrahydrofuran, 62 ml). After 15 min. stirring, the reaction mixture was quenched by addition of a saturated aqueous solution of ammonium chloride. The product was extracted into ethyl acetate; the combined organic phases were washed with brine, dried over sodium sulfate and concentrated under reduced pressure. Column chromatography afforded (7α,14β,15β,17α,20S)-3-methoxy-7-methyl-14,15-methylene-19-norpregna-1,3,5(10)-trien-20-ol (0.84 g) and (7α,14β,15β,17α,20R)-3-methoxy-7-methyl-14,15-methylene-19-norpregna-1,3,5(20-ol (0.23 g).

iia)—Following a procedure analogous to that described under vi of Example 1, (7α,14β,15β,17α,20S)-3-methoxy-7-methyl-14,15-methylene-19-norpregna-1,3,5(20-ol (0.48 g) was converted to (7α,14β,15β,17α,20S)-3-methoxy-7-methyl-14,15-methylene-19-norpregna-2,5(10)-dien-20-ol (0.59 g).

iib)—Following a procedure analogous to that described under vi of Example 1, (7α,14β,15β,17α,20R)-3-methoxy-7-methyl-14,15-methylene-19-norpregna-1,3,5(20-ol (0.23 g) was converted to (7α,14β,15β,17α,20R)-3-methoxy-7-methyl-14,15-methylene-19-norpregna-2,5(10)-dien-20-ol (0.11 g).

iiia)—Following a procedure analogous to that described under vii of Example 1, (7α,14β,15β,17α,20S)-3-methoxy-7-methyl-14,15-methylene-19-norpregna-2,5(10)-dien-20-ol (0.59 g) was converted to (7α,14β,15β,17α,20S)-20-hydroxy-7-methyl-14,15-methylene-19-norpregn-4-en-3-one (0.33 g). $^1$H NMR (CDCl$_3$) δ5.80 (m, 1H), 3.73 (m, 1H), 1.20 (s, 3H), 1.12 (d, 3H, J=6.3 Hz), 0.62 (d, 3H, J=7.1 Hz), 0.44 (dd, 1H, J=7.9 and 5.1 Hz), 0.26 (dd, 1H, J=5.1 and 3.1 Hz).

iiib)—Following a procedure analogous to that described under vii of Example 1, (7α,14β,15β,17α,20R)-3-methoxy-7-methyl-14,15-methylene-19-norpregna-2,5(10)-dien-20-ol (0.11 g) was converted to (7α,14β,15β,17α,20R)-20-hydroxy-7-methyl-14,15-methylene-19-norpregn-4-en-3-one (0.060 g). $^1$H NMR (CDCl$_3$) δ5.80 (m, 1H), 3.77 (m, 1H), 1.22 (d, 3H, J=6.7 Hz), 1.16 (s, 3H), 0.63 (d, 3H, J=7.1 Hz), 0.45 (dd, 1H, J=8.3 and 5.1 Hz), 0.23 (dd, 1H, J=5.1 and 3.5 Hz).

EXAMPLE 12

(7α,14β,15β,17α)-20-Hydroxy-7,20-dimethyl-14,15-methylene-19-norpregn-4-en-3-one

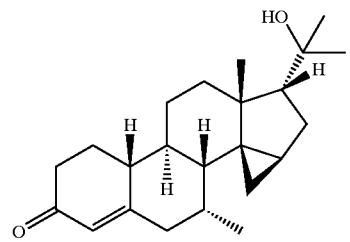

i)—Following a procedure analogous to that described under ii of Example 1, a mixture of (7α,14β,15β,17α,20S)-3-methoxy-7-methyl-14,15-methylene-19-norpregna-1,3,5(10)-trien-20-ol and (7α,14β,15β,17α,20R)-3-methoxy-7-methyl-14,15-methylene-19-norpregna-1,3,5(10)-trien-20-ol (Example 11, step i; 0.45 g, ratio 1:1) was converted to (7α,14β,15β,17α)-3-methoxy-7-methyl-14,15-methylene-19-norpregna-1,3,5(10)-trien-20-one (0.55 g).

ii)—Following a procedure analogous to that described under i of Example 11, the product obtained in the previous step (0.55 g) was converted to (7α,14β,15β,17α)-3-methoxy-7,20-dimethyl-14,15-methylene-19-norpregna-1,3,5(10)-trien-20-ol (0.26 g).

iii)—Following a procedure analogous to that described under vi of Example 1, the product obtained in the previous step (0.14 g) was converted to (7α,14β,15β,17α)-3-methoxy-7,20-dimethyl-14,15-methylene-19-norpregna-2,5(10)-trien-20-ol (0.14 g).

iv)—Following a procedure analogous to that described under vii of Example 1, the product obtained in the previous step (0.14 g) was converted to (7α,14β,15β,17α)-20-hydroxy-7,20-dimethyl-14,15-methylene-19-norpregn-4-en-3-one (0.050 g). $^1$H NMR (CDCl$_3$) δ5.80 (m, 1H), 1.32 (s, 3H), 1.21 (s, 3H), 1.20 (s, 3H), 0.64 (d, 3H, J=7.1 Hz), 0.42 (dd, 1H, J=7.9 and 5.1 Hz), 0.25 (dd, 1H, J=5.1 and 3.5 Hz).

EXAMPLE 13

(7α,14β,15β,17α,20S)-17-(1-Hydroxypropyl)-17-methyl-14,15-methyleneestr-4-en-3-one

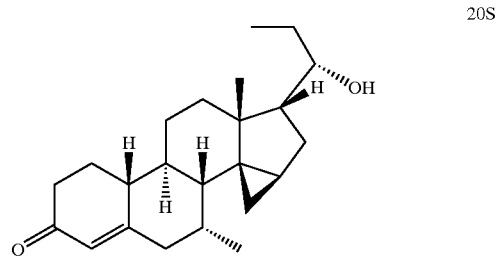

The title compound was prepared from (7α,14β,15β,17α)-3-methoxy-7-methyl-14,15-methyleneestra-1,3,5(10)-triene-17-carboxaldehyde (Example 1, step iv) using procedures described in Example 11. $^1$H NMR (CDCl$_3$) δ5.80 (m, 1H), 3.75 (m, 1H), 1.21 (s, 3H), 0.93 (t, 3H, J=7.9 Hz), 0.62 (d, 3H, J=7.1 Hz), 0.43 (m, 1H), 0.24 (m, 1H).

EXAMPLE 14

(7α,14β,15β,17α)-7-[(Acetyloxy)methyl)]-7-methyl-14,15-methyleneestr-4-en-3-one

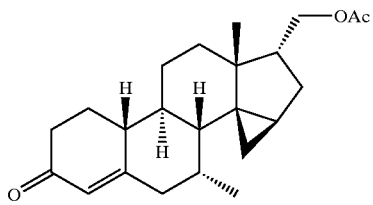

A solution of (7α,14β,15β,17α)-17-(hydroxymethyl)-7-methyl-14,15-methyleneestr-4-en-3-one (Example 1, 0.20 g) in a mixture of dry pyridine (1.76 ml) and dry tetrahydrofuran (8.8 ml) was treated with acetic anhydride (1.06 ml). The mixture was stirred at room temperature overnight and then quenched with water. After 1 h stirring the product was extracted into ethyl acetate. The combined organic phases were washed with brine, dried over sodium sulfate, and concentrated under reduced pressure to give (7α,14β,15β,17α)17-[(acetyloxy)methyl)]-7-methyl-14,15-methyleneestr-4-en-3-one (0.22 g). $^1$H NMR (CDCl$_3$) δ5.80 (t, 1H, J=2.8 Hz), 4.05 (dd, part A of AB system, 1H, J=11.0 and 6.3 Hz), 3.95 (dd, part B of AB system, 1H, J=11.0 and 7.1 Hz), 2.03 (s, 3H), 1.08 (s, 3H),. 0.62 (d, 3H, J=7.1 Hz), 0.48 (dd, 1H, J=8.3 and 5.1 Hz), 0.27 (dd, 1H, J=5.1 and 3.5 Hz).

EXAMPLE 15

Following a procedure analogous to that described under v of Example 1, and using the compounds of Example 1, 2, and 8, respectively, as starting material, the following products were prepared:

a)—(3β,7α,14β,15β,17α)-3-Hydroxy-7-methyl-14,15-methyleneestr-4-ene-17-methanol.

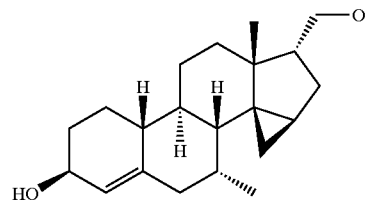

$^1$H NMR (CDCl$_3$) δ5.33 (bs, 1H), 4.21 (m, 1H), 3.67 (m, 1H), 3.48 (m, 1H), 1.05 (s, 3H), 0.58 (d, 3H, J=7.1 Hz), 0.45 (dd, 1H, J=7.9 and 5.1 Hz), 0.22 (dd, 1H, J=5.1 and 3.1 Hz).

b1)—(3α,7α,14β,15β,17α)-3-Hydroxy-7-methyl-14,15-methyleneestr-5(10)-ene-17-methanol.

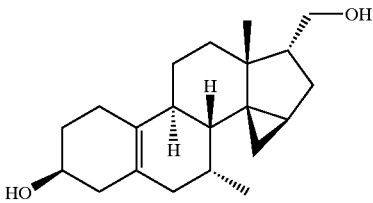

$^1$H NMR (CDCl$_3$) δ4.09 (m, 1H), 3.69 (m, 1H), 3.50 (m, 1H), 1.03 (s, 3H), 0.63 (d, 3H, J=7.1 Hz), 0.46 (dd, 1H, J=8.3 and 5.1 Hz), 0.24 (dd, 1H, J=5.1 and 3.5 Hz).

b2)—(3α,7α,14β,15β,17α)-3-Hydroxy-7-methyl-14,15-methyleneestr-5(10)-ene-17-methanol.

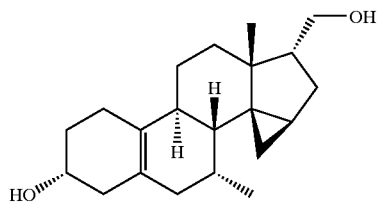

$^1$H NMR (CDCl$_3$) δ3.82 (m, 1H), 3.69 (m, 1H), 3.50 (m, 1H), 1.03 (s, 3H), 0.63 (d, 3H, J=7.1 Hz), 0.46 (dd, 1H, J=8.3 and 5.1 Hz), 0.24 (dd, 1H, J=5.1 and 3.5 Hz).

c1)—(3β,7α,14β,15β,17β)-3,17-Dihydroxy-7-methyl-14,15-methyleneestr-4-ene-17methanol.

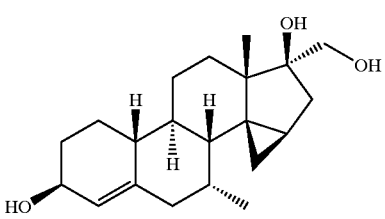

$^1$H NMR (CDCl$_3$) δ5.53 (m, 1H), 4.21 (m, 1H), 3.61 (dd, part A of AB system, 1H, J=10.6 and 4.7 Hz), 3.45 (dd, part B of AB system, 1H, J=10.6 and 5.9 Hz), 1.09 (s, 3H), 1.02 (dd, 1H, J=4.7 and 3.5 Hz), 0.56 (d, 3H, J=7.1 Hz), 0.54 (dd, 1H, J=8.3 and 4.7 Hz).

c2)—(3α,7α,15β,17β)-3,17-Dihydroxy-7-methyl-14,15-methyleneestr-4-ene-17-methanol.

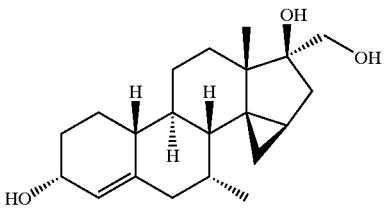

$^1$H NMR (CDCl$_3$) δ5.51 (m, 1H), 4.12 (m, 1H), 3.62 (dd, part A of AB system, 1H, J=10.6 and 4.7 Hz), 3.46 (dd, part B of AB system, 1H, J=10.6 and 5.9 Hz), 1.09 (s, 3H), 1.03 (dd, 1H, J=4.7 and 3.9 Hz), 0.59 (d, 3H, J=7.1 Hz), 0.54 (dd, 1H, J=8.6 and 4.7 Hz).

EXAMPLE 16

(7α, 14β,15β,17β)-17-Hydroxy-17-(methoxymethyl)-7-methyl-14,15-methyleneestr-4-en-3-one (reference compound 3)

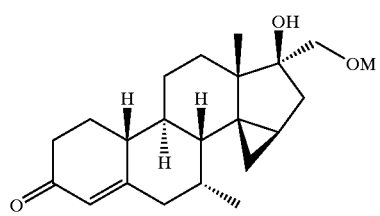

i)—A solution of (7α,14β,15β,17β)-3-methoxy-7-methyl-14,15-methylenespiroestra-1,3,5(10)-triene[17, 2']oxirane (Example 1, step iii; 2.0 g) in dry methanol (106 ml) was treated with sodium methoxide (6.91 g) and refluxed overnight. The reaction mixture was poured into ice-water and neutralized. The product was extracted into diethyl ether; the combined organic phases were washed with a saturated aqueous solution of sodium hydrogencarbonate and brine, dried over sodium sulfate, and concentrated under reduced pressure. Column chromatography gave (7α,14β,15β,17β)-3-methoxy-17-(methoxymethyl)-7-methyl-14,15-methyleneestra-1,3,5(10)-trien-17-ol (0.50 g).

ii)—Following a procedure analogous to that described under vi of Example 1, the product obtained in the previous step (0.50 g) was converted to (7α,14β,15β,17β)-3-methoxy-17-(methoxymethyl)-7-methyl-14,15-methyleneestra-2,5(10)-dien-17-ol (0.69 g).

iii)—Following a procedure analogous to that described under vii of Example 1, the product obtained in the previous step (0.69 g) was converted to (7α,14β,15β,17β)-17-hydroxy-17-(methoxymethyl)-7-methyl-14,15-methyleneestr-4-en-3-one (0.15 g). $^1$H NMR (CDCl$_3$) δ5.80 (m, 1H), 3.42 (d, part A of AB system, 1H, J=8.3 Hz), 3.33 (s, 3H), 3.16 (d, part B of AB system, 1H, J=8.3 Hz), 1.11 (dd, 1H, J=4.7 and 3.5 Hz), 1.09 (s, 3H), 0.60 (d, 3H, J=7.1 Hz), 0.50 (dd, 1H, J=8.3 and 4.7 Hz).

EXAMPLE 17
(7α,14β,15β,17β)-17-(Chloromethyl)-17-hydroxy-7-methyl-14,15-methyleneestr-4-en-3-one (reference compound 4)

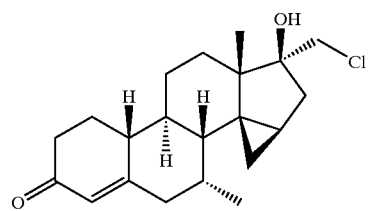

i)—Following a procedure analogous to that described under vi of Example 1, (7α,14β,15β)-3-methoxy-7-methyl-14,15-methyleneestra-1,3,5(10)-trien-17-one (Example 1, step ii; 8.0 g) was converted to (7α,14β,15β,17α)-3-methoxy-7-methyl-14,15-methyleneestra-2,5(10)-dien-17-ol (8.0 g).

ii)—Following a procedure analogous to that described under vii of Example 1, the product obtained in the previous step (8.0 g) was converted to (7α,14β,15β,17α)-17-hydroxy-7-methyl-14,15-methyleneestr-4-en-3-one (2.51 g).

iii)—Following a procedure analogous to that described under ii of Example 1, the product obtained in the previous step (2.51 g) was converted to (7α,14β,15β)-7-methyl-14,15-methyleneestr-4-ene-3,17-dione (2.23 g).

iv)—Boron trifluoride diethyl etherate (0.27 ml) was added to a mixture of the product obtained in the previous step (2.23 g), 1,2-ethanedithiol (0.67 ml), dry tetrahydrofuran (10 ml), and dry methanol (20 ml), cooled to 0° C. After 2 h stirring at room temperature, the reaction mixture was poured into water. The product was extracted into ethyl acetate; the combined organic phases were washed with aqueous sodium hydroxide (10%) and brine, dried over sodium sulfate and concentrated under reduced pressure. Column chromatography gave (7α,14β,15β)-7-methyl-14,15-methyleneestr-4-ene-3,17-dione cyclic 3-(1,2-ethanediyl dithioacetal) (2.68 g). The product was used in the next step without further purification.

v)—Following a procedure analogous to that described under iii of Example 1, the product obtained in the previous step (2.68 g) was converted to (7α,14β,15β,17β)-3-[(2-mercaptoethyl)thio]-7-methyl-14,15-methylenespiroestra-3,5-diene[17,2']oxirane (2.81 g).

vi)—A solution of the product obtained in the previous step (0.50 g) in dimethylformamide (7.3 ml) was treated with concentrated hydrochloric acid (0.73 ml). After 1 h stirring at room temperature, the reaction mixture was poured into a saturated aqueous solution of sodium hydrogencarbonate and the product was extracted into ethyl acetate. The combined organic phases were washed with brine, dried over sodium sulfate and concentrated under reduced pressure. Column chromatography afforded (7α,14β,15β,17α)-17-(chloromethyl)-17-hydroxy-7-methyl-14,15-methyleneestr-4-en-3-one (0.035 g). $^1$H NMR (CDCl$_3$) δ5.81 (m, 1H), 3.67 (d, part A of AB system, 1H, J=11.0 Hz), 3.58 (d, part B of AB system, 1H, J=11.0 Hz), 1.17 (dd, 1H, J=5.1 and 3.5 Hz), 1.15 (s, 3H), 0.60 (d, 3H, J=6.7 Hz), 0.54 (dd, 1H, J=8.3 and 5.1 Hz).

EXAMPLE 18
Biological Results

The compounds according to the invention and four reference compounds were tested for drogenic activity (the procedures for which have been described above) and rated according the following scheme:

| | | | |
|---|---|---|---|
| (−) | no androgenic activity found: | (+) | androgenic activity found; |
| (++) | high androgenic activity; | (+++) | excellent androgenic activity; |
| (n.d.) | no data available | (pro) | prodrug |

I. Compounds of the Invention

| Ex. | R$_1$ | R$_2$ | R$_3$ | R$_4$ | R$_5$ | R$_6$ | R$_7$ | R$_8$ | R$_9$ | R$_{10}$ | R$_{11}$ | Uns. | Res. |
|---|---|---|---|---|---|---|---|---|---|---|---|---|---|
| 1 | oxo | H | Me | H | Me | H | H | H | H | H | H | Δ$^4$ | +++ |
| 2 | oxo | H | Me | H | Me | H | H | H | H | H | H | Δ$^{5(10)}$ | + |
| 3 | oxo | H | Me | H | Me | H | H | H | H | H | H | Δ$^{4,9}$ | ++ |
| 4 | oxo | Me | Me | H | Me | H | H | H | H | H | H | Δ$^4$ | ++ |
| 5 | oxo | H | Et | H | Me | H | H | H | H | H | H | Δ$^4$ | ++ |
| 6 | oxo | H | Me | H | Et | H | H | H | H | H | H | Δ$^4$ | +++ |

-continued

| Ex. | $R_1$ | $R_2$ | $R_3$ | $R_4$ | $R_5$ | $R_6$ | $R_7$ | $R_8$ | $R_9$ | $R_{10}$ | $R_{11}$ | Uns. | Res. |
|---|---|---|---|---|---|---|---|---|---|---|---|---|---|
| 7 | oxo | H | Me | H | Me | H | 16β-Me | H | H | H | H | $\Delta^4$ | + |
| 8 | oxo | H | Me | H | Me | H | H | OH | H | H | H | $\Delta^4$ | + |
| 9a | oxo | H | Me | H | Me | H | H | F | H | H | Ac | $\Delta^4$ | ++ |
| 9b | oxo | H | Me | H | Me | H | H | F | H | H | H | $\Delta^4$ | ++ |
| 10 | oxo | H | Me | H | Me | H | H | F | H | H | Ac | $\Delta^{5(10)}$ | + |
| 11a | oxo | H | Me | H | Me | H | H | H | 20S—Me | H | H | $\Delta^4$ | ++ |
| 11b | oxo | H | Me | H | Me | H | H | H | H | 20R—Me | H | $\Delta^4$ | + |
| 12 | oxo | H | Me | H | Me | H | H | H | Me | Me | H | $\Delta^4$ | + |
| 13 | oxo | H | Me | H | Me | H | H | H | 20S—Et | H | H | $\Delta^4$ | + |
| 14 | oxo | H | Me | H | Me | H | H | H | H | H | Ac | $\Delta^4$ | ++ |
| 15a | 3β-OH | H | Me | H | Me | H | H | H | H | H | H | $\Delta^4$ | +++ |
| 15b1 | 3β-OH | H | Me | H | Me | H | H | H | H | H | H | $\Delta^{5(10)}$ | pro |
| 15b2 | 3α-OH | H | Me | H | Me | H | H | H | H | H | H | $\Delta^{5(10)}$ | Pro |
| 15c1 | 3β-OH | H | Me | H | Me | H | H | OH | H | H | H | $\Delta^4$ | + |
| 15c2 | 3α-OH | H | Me | H | Me | H | H | OH | H | H | H | $\Delta^4$ | + |

II. Reference Compounds

| Compound | Result |
|---|---|
| (14β,15β,17β)-17-hydroxy-17-(methoxymethyl)-14,15-methyleneestr-4-en-3-one (reference compound 1, WO 99/67276, J 1222) | — |
| (14β,15β,17β)-17-(chloromethyl)-17-hydroxy-14,15-methyleneestr-4-en-3-one (reference compound 2, WO 99/67276, J 1364) | — |
| (7α,14β,15β,17β)-17-hydroxy-17-(methoxymethyl)-7-methyl-14,15-methyleneestr-4-en-3-one (reference compound 3, Example 16) | — |
| (7α,14β,15β,17β)-17-(chloromethyl)-17-hydroxy-7-methyl-14,15-methyleneestr-4-en-3-one (reference compound 4, Example 17) | — |

What is claimed is:

1. A compound satisfying the structural formula

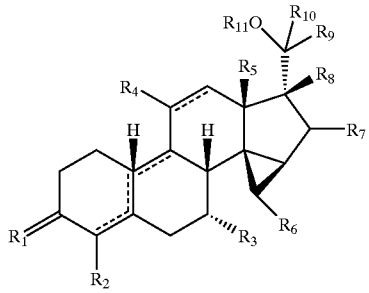

wherein
$R_1$ is O, (H,H), (H,OR), NOR, with R being hydrogen, $(C_{1-6})$ alkyl, $(C_{1-6})$ acyl;
$R_2$ is hydrogen, or $(C_{1-6})$ alkyl;
$R_3$ is hydrogen; or $R_3$ is $(C_{1-6})$ alkyl $(C_{2-6})$ alkenyl, or $(C_{2-6})$ alkynyl, each optionally substituted by halogen;
$R_4$ is hydrogen, $(C_{1-6})$ alkyl, or $(C_{2-6})$ alkenyl;
$R_5$ is $(C_{1-6})$ alkyl;
$R_6$ is hydrogen, halogen, or $(C_{1-4})$ alkyl;
$R_7$ is hydrogen, or $(C_{1-6})$ alkyl;
$R_8$ is hydrogen, hydroxy, $(C_{1-6})$ alkoxy, halogen, or $(C_{1-6})$ alkyl;
$R_9$ and $R_{10}$ are independently hydrogen; or $R_9$ and $R_{10}$ are independently $(C_{1-6})$ alkyl, $(C_{2-6})$ alkenyl, $(C_{3-6})$ cycloalkyl, $(C_{5-6})$ cycloalkenyl, or $(C_{2-6})$ alkynyl, each optionally substituted by $(C_{1-4})$ alkoxy, or halogen;
$R_{11}$ is hydrogen, $SO_3H$, $(C_{1-15})$ acyl; and the dotted lines indicate optional bonds, selected from a $\Delta^4$, $\Delta^{5(10)}$, or $\Delta^{11}$ double bond, or a $\Delta^{4,9}$ or $\Delta^{4,11}$ diene system.

2. A compound according to claim 1, characterized in that the substituent $R_1$ is O.

3. A compound according to claim 1, wherein the dotted lines indicate a $\Delta^4$ double bond.

4. A compound according to claim 1, wherein $R_4$ is 7α-methyl.

5. the compound (7α,14β,15β,17α)-17-(hydroxymethyl)-7-methyl-14,15-methyleneestr-4-en-3-one.

6. A pharmaceutical composition having androgenic activity comprising an efective amount of a compound according to claim 1 and a pharmaceutically acceptable auxilary.

7. A kit providing for hormonal contraception in a male, comprising a sterilitant and an androgen, wherein the androgen is a compound according to claim 1.

8. A method of treatment for a human having androgen insufficiency comprising administering an effective amount of a compound according to claim 1.

9. The method according to claim 8, wherein the human is a male, and the androgen insufficiency is the result of the administration of a sterilitant to said male in the course of a method of male contraception.

* * * * *

UNITED STATES PATENT AND TRADEMARK OFFICE
CERTIFICATE OF CORRECTION

PATENT NO. : 6,706,700 B2
DATED : March 16, 2004
INVENTOR(S) : Leysen et al.

It is certified that error appears in the above-identified patent and that said Letters Patent is hereby corrected as shown below:

Title page,
Item [73], Assignee, should read: -- Akzo Nobel N.V. (NL) --

Signed and Sealed this

Eighth Day of June, 2004

JON W. DUDAS
*Acting Director of the United States Patent and Trademark Office*